United States Patent [19]

Förster et al.

[11] 4,399,285
[45] Aug. 16, 1983

[54] TETRAZOLYLOXYACETIC ACID AMIDES, PIPERIDIDES AND PERHYDRO AZEPINIDES

[75] Inventors: Heinz Förster; Wolfgang Hofer; Fritz Maurer; Volker Mues, all of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 200,171

[22] Filed: Oct. 24, 1980

[30] Foreign Application Priority Data

Nov. 17, 1979 [DE] Fed. Rep. of Germany ....... 2946432

[51] Int. Cl.$^3$ ................. C07D 257/02; C07D 401/12; C07D 403/12
[52] U.S. Cl. .................................... 546/210; 548/251; 548/468; 544/366; 546/164; 546/148; 546/162; 546/17; 71/88; 71/94; 71/95; 71/96
[58] Field of Search .................. 548/253, 251; 546/210

[56] References Cited
FOREIGN PATENT DOCUMENTS 2637886 10/1977 Fed. Rep. of Germany .
5501 11/1979 Fed. Rep. of Germany .

*Primary Examiner*—Donald G. Daus
*Assistant Examiner*—D. B. Springer

*Attorney, Agent, or Firm*—Felfe & Lynch

[57] ABSTRACT

Tetrazolyloxycarboxylic acid amide compound of the formula

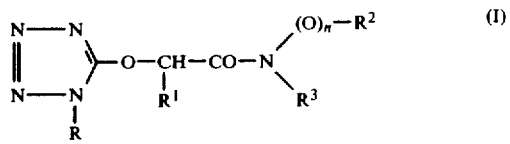

wherein
R is an optionally substituted radical selected from the group consisting of alkyl or aryl,
$R^1$ is hydrogen or alkyl,
n is 0 or 1, and
$R^2$ and $R^3$ are individually selected from hydrogen or optionally substituted radicals selected from the group consisting of alkyl, alkenyl, alkynyl, cycloalkyl, cycloalkenyl, aralkyl and aryl, with the proviso that when n is 0,
$R^2$ and $R^3$, together with the nitrogen atom to which they are bonded, form an optionally substituted, optionally partially unsaturated and optionally benzofused monocyclic or bicyclic radical which optionally contains one or more further hetero-atoms
are effective herbicides.

10 Claims, No Drawings

TETRAZOLYLOXYACETIC ACID AMIDES, PIPERIDIDES AND PERHYDRO AZEPINIDES

This invention relates to certain new tetrazolyloxycarboxylic acid amide compounds, to herbicidal compositions containing them and to methods of combating undesired vegetation utilizing such compounds.

It has already been disclosed that certain phenoxycarboxylic acid amides, for example 2,4-dichlorophenoxyacetic acid amide, have a herbicidal action (see French Patent Specification No. 1,313,840). However, the phenoxycarboxylic acid amides known as herbicides have only a slight action against graminaceous weeds when applied in the customary amounts, and cannot be used for combating weeds in various dicotyledon cultures because of their deficient selectivity.

The present invention now provides, as new compounds, the tetrazolyloxycarboxylic acid amides of the general formula

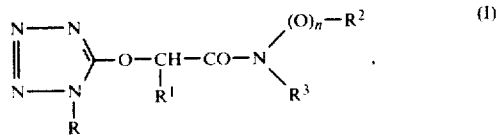

in which

R represents optionally substituted alkyl or optionally substituted aryl,

R¹ represents hydrogen or alkyl, n represents zero or 1 and

R² and R³, which can be identical or different, each represent hydrogen or an optionally substituted radical from the series alkyl, alkenyl, alkynyl, cycloalk(en)yl, aralkyl and aryl, or R² and R³ provided that n represents zero, form, together with the nitrogen atom to which they are bonded, an optionally substituted, optionally partially unsaturated and optionally benzo-fused monocyclic or bicyclic radical, which optionally contains one or more further hetero-atoms.

The invention also provides a process for the preparation of a tetrazolyloxycarboxylic acid amide of the general formula (I), in which an α-hydroxycarboxylic acid amide of the general formula

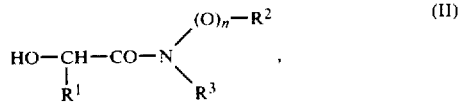

in which n, R¹, R² and R³ have the meanings indicated above, is reacted with a halogenotetrazole of the general formula

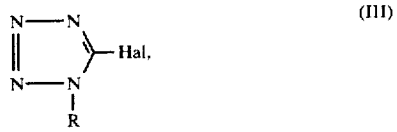

in which

R has the meaning indicated above and

Hal represents chlorine, bromine or iodine, if appropriate in the presence of an acid acceptor and if appropriate using a diluent.

The tetrazolyloxycarboxylic acid amides of the formula (I) are distinguished by a powerful herbicidal activity.

Surprisingly, the tetrazolyloxycarboxylic acid amides according to this invention exhibit a considerably better and different type of herbicidal action than the phenoxycarboxylic acid amides known from the state of the art. It is particularly surprising that, coupled with their good toleration by useful plants, the compounds according to the invention also exhibit a very good action against graminaceous weeds, in addition to their powerful action against dicotyledon weeds, whilst structurally similar phenoxy-alkanecarboxylic acid derivatives, for example 2,4-dichlorophenoxy-acetamide, have only a slight action against Graminaceae. They are also suitable for selectively combating weeds in beet, soya bean, cotton, maize, rice and other varieties of cereal.

The preferred tetrazolyloxycarboxylic acid amides of the formula (I) are those in which R represents phenyl, which optionally carries one or more substituents selected from halogen, cyano, nitro and optionally halogen-substituted radicals from the series $C_1$–$C_4$-alkyl, $C_1$–$C_4$-alkoxy, $C_1$–$C_4$-alkylthio and $C_1$–$C_2$-alkylenedioxy, R¹ represents hydrogen or methyl, n represents zero or 1 and R² represents alkyl, alkoxyalkyl, alkenyl or alkynyl, in each case with up to 10 carbon atoms, or, provided that n represents zero, cyanoalkyl or alkylthioalkyl, in either case with up to 10 carbon atoms, cycloalkyl with 3 to 12 carbon atoms, optionally halogen-subsituted benzyl, optionally halogen-substituted phenethyl, or phenyl which is optionally substituted by one or more optionally halogen-substituted radicals selected from the series $C_1$–$C_4$-alkyl, $C_1$–$C_4$-alkoxy and $C_1$–$C_4$-alkylthio, and R³ represents alkyl, alkenyl, alkynyl, alkoxyalkyl, alkylthioalkyl or cyanoalkyl, in each case with up to 10 carbon atoms, cycloalkyl with 3 to 12 carbon atoms, an optionally halogen-substituted benzyl, phenethyl or naphthyl radical, or phenyl which optionally carries one or more substituents selected from halogen, cyano, nitro and optionally halogen-substituted radicals from the series $C_1$–$C_4$-alkyl, $C_1$–$C_4$-alkoxy and $C_1$–$C_4$-alkylthio, or R² and R³, provided that n represents zero, form, together with the nitrogen atom to which they are bonded, an optionally partially unsaturated and/or benzo-fused monocyclic or bicyclic radical which has up to 15 carbon atoms and is optionally substituted by 1 to 3 alkyl groups with in each case 1 to 5 carbon atoms, or by two geminal alkoxy groups with in each case 1 to 3 carbon atoms, or is optionally substituted by a dioxolanylidene or dioxanylidene radical linked in a spirocyclic manner, or R² and R³, together with the nitrogen atom to which they are bonded, form a monocyclic radical which has up to 5 carbon atoms, is optionally substituted by 1 to 3 alkyl groups with in each case 1 to 5 carbon atoms, by phenyl which is optionally substituted by $C_1$–$C_4$-alkyl, $C_1$–$C_4$-alkoxy, halogen, $C_1$–$C_2$-halogenoalkyl or nitro, by benzyl or by phenethyl, is saturated and contains a further nitrogen atom, oxygen atom or sulphur atom.

Particularly preferred compounds of the formula (I) are those in which

R represents phenyl, which optionally carries one or more substituents selected independently from chlorine, nitro, methyl and trifluoromethyl, R$^1$ represents hydrogen, n represents zero or 1 and R$^2$ represents C$_1$-C$_6$-alkyl, C$_1$-C$_4$-alkoxy-ethyl, allyl, propargyl, 1-methyl-propargyl or 1,1-dimethyl-propargyl, or, provided n represents zero, cyanomethyl, cyclopentyl, cyclohexyl, benzyl or phenyl, and R$^3$ represents C$_1$-C$_6$-alkyl, C$_1$-C$_4$-alkoxy-ethyl, allyl, propargyl, 1-methyl-propargyl, 1,1-dimethyl-propargyl, cyanomethyl, cyclopentyl, cyclohexyl, benzyl or naphthyl, or phenyl which optionally carries one or more substituents selected independently from methyl, chlorine, cyano, nitro and methoxy, or R$^2$ and R$^3$, provided n represents zero, together with the nitrogen atom to which they are bonded, represent pyrrolidyl, monoalkyl- or dialkyl-pyrrolidyl with 1 to 3 carbon atoms per alkyl group, morpholinyl or dialkyl-morpholinyl with 1 to 3 carbon atoms per alkyl group, piperidyl, monoalkyl-, dialkyl- or trialkyl-piperidyl with 1 to 3 carbon atoms per alkyl group, 4,4-dialkoxy-piperidyl with 1 to 3 carbon atoms per alkoxy group, spiro-substituted piperidyl of the general formula

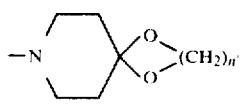

wherein n' represents 2 or 3, or perhydroazepinyl (hexamethyleneimino radical), trimethyl-perhydroazepinyl, the heptamethyleneimino radical, the dodecamethyleneimino radical, 1,2,3,4-tetrahydroindolyl, monoalkyl-, dialkyl- or trialkyl-1,2,3,4-tetrahydroindolyl with up to 3 carbon atoms per alkyl group, perhydroindolyl, monoalkyl-, dialkyl- or trialkyl-perhydroindolyl with 1 to 3 carbon atoms per alkyl group, 1,2,3,4-tetrahydroquinolyl or 1,2,3,4-tetrahydro-iso-quinolyl, monoalkyl-, dialkyl or trialkyl-1,2,3,4-tetrahydro-quinolyl or -isoquinolyl with 1 to 3 carbon atoms per alkyl group, perhydroquinolyl pehydro-isoquinolyl, monoalkyl-, dialkyl- or trialkylperhydroquinolyl or -perhydroisoquinolyl with 1 to 3 carbon atoms per alkyl group, perhydrothiazolyl, perhydrooxazolyl, perhydrooxazinyl, the radical

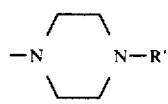

wherein

R' represents C$_1$-C$_4$-alkyl, phenyl which optionally carries one or more substituents selected independently from C$_1$-C$_2$-alkyl, C$_1$-C$_2$-alkoxy, fluorine, chlorine, bromine, trifluoromethyl and nitro, or benzyl or phenethyl, or the radical wherein X represents hydrogen or methyl

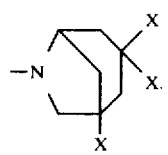

If, for example, 5-chloro-1-phenyl-(1-H)-tetrazole and hydroxyacetic acid piperidine are used as starting substances, the course of the reaction in the process according to the invention can be represented by the following equation:

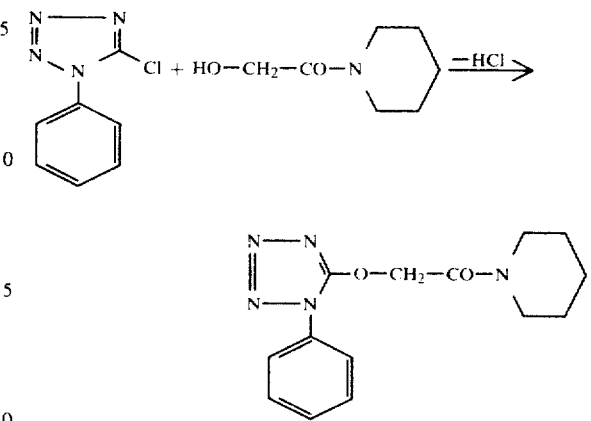

The formula (II) provides a general definition of the α-hydroxy-carboxylic acid amides to be used as starting substances. In this formula, n, R$^1$, R$^2$ and R$^3$ preferably have those meanings which have already been mentioned as preferred within the scope of the substituent definitions for the formula (I).

The following α-hydroxy-carboxylic acid amides may be mentioned as examples of starting substances of the formula (II): N-methoxy-N-methyl-, N-ethoxy-N-methyl-, N-n-propoxy-N-methyl-, N-iso-propoxy-N-methyl-, N-ethoxy-N-ethyl-, N-n-propoxy-N-ethyl-, N-iso-propoxy-N-ethyl-, N-n-propoxy-N-n-propyl-, N-iso-propoxy-N-isopropyl-, N-iso-propoxy-N-n-propyl-, N-methoxy-N-ethyl-, N-methoxy-N-n-propyl-, N-methoxy-N-iso-propyl-, N-methoxy-N-n-butyl-, N-methoxy-N-isobutyl-, N-methoxy-N-sec.-butyl-, N-methoxy-N-sec.-hexyl-, N-ethoxy-N-n-propyl-, N-ethoxy-N-isopropyl-, N-(2-ethoxy-ethoxy)-n-methyl-, N-(2-ethoxy-ethoxy)-N-ethyl-, N-(2-ethoxy-ethoxy)-N-n-propyl-, N-(2-ethoxy-ethoxy)-N-isopropyl-, N-(2-ethoxy-ethoxy)-N-cyclohexyl-, N-allyloxy-N-allyl-, N-allyloxy-N-methyl-, N-allyloxy-N-ethyl-, N-allyloxy-N-n-propyl-, N-allyloxy-N-isopropyl-, N-allyloxy-N-n-butyl-, N-allyloxy-N-isobutyl-, N-allyloxy-N-sec.-butyl-, N-methoxy-N-cyclopentyl-, N-methoxy-N-cyclohexyl-, N-methoxy-N-(2-ethoxy-ethyl)-, N-ethoxy-N-(2-ethoxy-ethyl)-, N-(2-ethoxy-ethoxy)-N-(2-ethoxy-ethyl)- and N-(2-ethoxy-ethoxy)-N-sec.-hexyl-hydroxy-acetamide, and hydroxyacetic acid dimethylamide, diethylamide, di-n-propyl-amide, di-iso-propylamide, N-methyl-N-iso-propylamide, N-methyl-N-iso-butylamide, N-methyl-N-sec.-butylamide, di-(2-ethyl-hexyl)-amide, N-methyl-N-(2-cyano-ethyl)-amide, di-(2-methoxy-ethyl)-amide, di-allylamide, N-methyl-N-propargylamide, N-methyl-N-(1-methyl-propargyl)-amide, dipropargylamide, N-methyl-N-cyclopentylamide, N-methyl-N-cyclohexylamide, N-methyl-anilide, N-methyl-N-(2-nitro-phenyl)-, N-methyl-N-(3-nitro-phenyl)- and N-methyl-N-(4-nitro-phenyl)-amide, N-methyl-N-(2-chlorophenyl)-, N-methyl-N-(3-chloro-phenyl)- and N-methyl-N-(4-chloro-phenyl)-amide, N-methyl-N-(3-nitro-6-methyl-phenyl)-amide, N-ethyl-anilide, N-ethyl-N-(2-nitro-phenyl)-, N-ethyl-N-(3-nitro-phenyl)- and N-ethyl-N-(4-nitro-phenyl)-amide, N-ethyl-N-(2-chlorophenyl)-, N-ethyl-N-(3-chloro-phenyl)- and N-ethyl-N-(4-chloro-phenyl)-amide, N- ethyl-N-(3-nitro-6-methyl-phenyl)-amide, N-propyl-anilide, N-propyl-N-(2-nitro-phenyl)-; N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methyl-phenyl)- and N-propyl-N-(4-methyl-phenyl)-amide, N-propyl-N-(3-nitro-6-methyl-phenyl)-amide, N-butyl-anilide, N-butyl-N-(2-nitro-phenyl)-, N-butyl-N-(3-nitro-phenyl)- and N-butyl-N-(B 4-nitro-phenyl)-amide, N-butyl-N-(2-chloro-phenyl)-, N-butyl-N-(3-chloro-phenyl)- and N-butyl-N-(4-chloro-phenyl)-amide, N-butyl-N-(2-methylphenyl)-, N-butyl-N-(3-methyl-phenyl)- and N-butyl-N-(4-methyl-phenyl)-amide, N-butyl-N-(3-nitro-6-methyl-phenyl)-amide, N-isobutyl-anilide, N-iso-butyl-N-(2-nitro-phenyl)-, N-iso-butyl-N-(3-nitro-phenyl)- and N-iso-butyl-N-(4-nitro-phenyl)-amide, N-iso-butyl-N-(2-chloro-phenyl)-, N-isobutyl-N-(3-chloro-phenyl)- and N-iso-butyl-N-(4-chloro-phenyl)-amide, N-iso-butyl-N-(2-methyl-phenyl)-, N-iso-butyl-N-(3-methyl-phenyl)- and N-iso-butyl-N-(4-methylphenyl)-amide, N-iso-butyl-N-(3-nitro-6-methyl-phenyl)-amide, -N-methyl-N-naphth-1-ylamide, N-methyl-N-naphth-2-ylamide, N-ethyl-N-naphth-1-ylamide, N-ethyl-N-naphth-2-ylamide, N-n-propyl-N-naphth-2-ylamide, N-iso-propyl-N-naphth-2-ylamide, N-n-butyl-N-naphth-2-ylamide, N-iso-butyl-N-naphth-2-ylamide, dibenzylamide, N-methyl-N-benzylamide, N-ethyl-N-benzylamide, N-propyl-N-benzylamide, N-butyl-N-benzylamide, pyrrolidide, 2-methyl-pyrrolidide, morpholide, 3,5-dimethyl-morpholide, piperidide, 2-methyl-piperidide, 4-methyl-piperidide, 2,4-dimethyl-piperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, 1,2,3,4-tetrahydroindolide, 2-methyl-1,2,3,4-tetrahydroquinolide, perhydroindolide, 2-methyl-perhydroindole, 2,2-dimethyl-perhydroindolide, 1,2,3,4-tetrahydroquinolide, 2-methyl-1,2,3,4-tetrahydroquinolide, perhydroquinolide, 2-methyl-perhydroquinolide, 1,2,3,4-tetrahydroisoquinolide and perhydroisoquinolide.

Some of the α-hydroxy-carboxylic acid amides of the formula (II) are known (see U.S. Pat. No. 3,399,988; and DE-OS's (German Published Specifications) Nos. 2,201,432 and 2,647,481). The compounds (II) can be prepared starting from α-chlorocarboxylic acid chlorides, as outlined in the following equations:

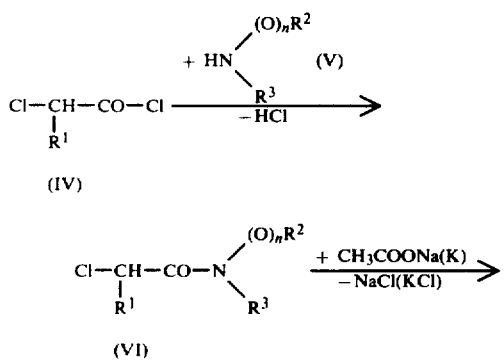

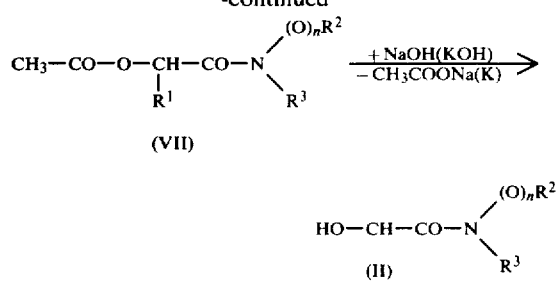

For this preparation, the α-chlorocarboxylic acid chlorides of the general formula (IV), which are known from the literature, are first converted into the corresponding chlorocarboxylic acid amides of the general formula (VI) with amines of the formula (V), n, $R^1$, $R^2$ and $R^3$ having the meanings indicated above, if appropriate in the presence of an acid-binding agent, for example triethylamine, and if appropriate using an inert diluent, for example 1,2-dichloroethane, at temperatures between $-20°$ and $100°$ C., preferably between $-10°$ and $50°$ C. The products are worked up by customary methods, by washing the mixture with water, drying the organic phase and distilling off the solvent.

The compounds of the formula (VI) are reacted with sodium acetate or potassium acetate, if appropriate using a diluent, for example acetic acid or dimethylsulphoxide, at temperatures between $20°$ and $150°$ C., preferably between $50°$ and $120°$ C., to give the corresponding α-acetoxy-carboxylic acid amides of the formula (VII). If the products are obtained as crystals, they are isolated by filtration. Otherwise, the working up is carried out by customary methods, for example by distilling off the solvent in vacuo, taking up the residue in methylene chloride, washing the methylene chloride mixture with water and distilling off the solvent.

The compounds of the formula (VII) can be deacylated to give the compounds of the formula (II) by reaction with aqueous-alcoholic sodium hydroxide solution or potassium hydroxide solution at temperatures between $0°$ and $100°$ C., preferably between $10°$ and $50°$ C. To isolate the products, the solvents are distilled off in vacuo, the residue is extracted with an organic solvent, for example methylene chloride or ethyl acetate, the solution is dried and the solvent is distilled off.

Formula (III) provides a definition of the halogenotetrazoles also to be used as starting substances. In this formula, R preferably represents those radicals which have already been mentioned as preferred within the scope of the substituent definitions of the formula (I), and Hal preferably represents chlorine or bromine.

Examples of starting substances of the formula (III) which may be mentioned are: 5-chloro- and 5-bromo-1-phenyl-(1H)-tetrazole, 5-chloro- and 5-bromo-1-(4-chloro-2-methyl-phenyl)-(1H)-tetrazole, 5-chloro- and 5-bromo-1-(2-chloro-6-methyl-phenyl)-(1H)-tetrazole, 5-chloro- and 5-bromo-1-(3-nitro-phenyl)-(1H)-tetrazole, 5-chloro- and 5-bromo-1-(4-methyl-phenyl)-(1H)-tetrazole, 5-chloro- and 5-bromo-1-(2,5-dichloro-phenyl)-(1H)-tetrazole, 5-chloro- and 5-bromo-1-(3,4-dichloro-phenyl)-(1H)-tetrazole, 5-chloro- and 5-bromo-1-(3-trifluoromethylphenyl)-(1H)-tetrazole, 5-chloro- and 5-bromo-1-(2-methyl-phenyl)-(1H)-tetrazole, 5-chloro- and 5-bromo-1-(3-methyl-phenyl)-(1H)-tetrazole, 5-chloro- and 5-bromo-1-(3,4-dimethylphenyl)-(1H)-tetrazole and 5-chloro- and 5-bromo-1-(2,4-dimethylphenyl)-(1H)-tetrazole.

Halogenotetrazoles of the formula (III) are already known (see DE-AS (German Published Specification) No. 1,251,327 and British Patent Specification 1,128,025). Chlorotetrazoles of the formula (III) are obtained, for example, by reacting isocyanide dichlorides of the general formula

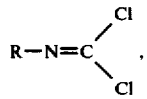  (VII)

in which R has the meaning indicated above, with sodium azide, if appropriate in the presence of diluents, for example water and acetone, at temperatures between 10° and 100° C.

The products, which are obtained as crystals, are isolated by vacuum filtration, if appropriate after dilution of the mixture with water.

The process for the preparation of the azolyloxycarboxylic acid amides of the present invention is preferably carried out using a suitable solvent or diluent. Possible solvents or diluents are virtually any of the organic solvents. These include, as preferences, alcohols, such as methanol, ethanol, n- and iso-propanol and n-, iso-, sec.- and tert.-butanol; ethers, such as diethyl ether, dibutyl ether, tetrahydrofuran and dioxan; ketones, such as acetone, methyl ethyl ketone, methyl isopropyl ketone and methyl isobutyl ketone; nitriles, such as acetonitrile and propionitrile; and the highly polar solvents dimethylformamide, dimethylsulphoxide, sulpholane and hexamethylphosphoric acid triamide.

Virtually any of the acid-binding agents which can customarily be used can be employed as acid acceptors: these acid-binding agents include, as preferences, alkali metal hydroxides or oxides, such as sodium hydroxide or potassium hydroxide; alkaline earth metal hydroxides or oxides, such as calcium hydroxide; alkali metal carbonates and alkaline earth metal carbonates, such as sodium carbonate, potassium carbonate and calcium carbonate; alkali metal alcoholates, such as sodium methylate, ethylate and tert.-butylate and potassium methylate, ethylate and tert.-butylate; and aliphatic, aromatic or heterocyclic amines, such as triethylamine, dimethylaniline, dimethylbenzylamine, pyridine, diazabicyclooctane and diazabicycloundecene.

The reaction temperature can be varied within a substantial range. In general, the reaction is carried out between −50° and +150° C., preferably at from −20° to +100° C.

The process according to the invention is in general carried out under normal pressure.

In carrying out the process according to the invention, 1.0 to 1.5 moles of α-hydroxy-carboxylic acid amide of the formula (II) are preferably employed per mole of halogenoazole of the formula (III). The reaction is in general carried out in a suitable diluent, and the reaction mixture is stirred at the required temperature for several hours.

The products are isolated by customary methods: some of the diluent is distilled off, if appropriate, under reduced pressure and the remainder of the reaction mixture is poured into water. If the products are thereby obtained as crystals, they are isolated by filtration. Otherwise, the organic products are extracted with a water-immiscible solvent, for example toluene or methylene chloride; after washing and drying, the solvent is then distilled off from the organic phase in vacuo. The products which remain are characterised by their melting point or their refractive index.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapsis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

Besides a very good action against graminaceous weeds, including Cyperus, the active compounds according to the invention also exhibit, in particular, a good herbicidal action against broad-leaved weeds. The active compounds according to the invention can be used selectively in various crops, for example in beet, soya bean, cotton, maize, rice and other varieties of cereal. Individual active compounds are particularly suitable as selective herbicides in beet, cotton and cereals.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules or inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within substantial ranges. It depends essentially on the nature of the desired effect. In general, the amounts used are between 0.01 and 10 kg of active compound per hectare, preferably between 0.1 and 8 kg/ha.

Some of the active compounds according to the invention also have a growth-regulating action when applied in certain concentrations.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

In this Example, the compounds according to the present invention are each identified by the number (given in brackets) of the corresponding preparative Example, which will be found later in this specification.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

In this test, for example, the following compounds exhibited an excellent action: (1), (3), (4), (8), (14), (15), (16), (21), (28), (30), (31), (36), (97), (98), (99), (100), (101) and (102).

PREPARATIVE EXAMPLES

Example 1

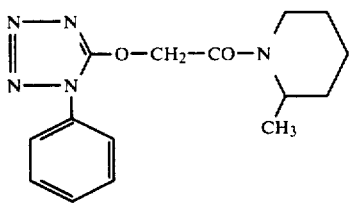
(1)

12.6 g (0.08 mol) of hydroxyacetic acid 2-methyl-piperidide and 14.4 g (0.08 mol) of 5-chloro-1-phenyl-(1H)-tetrazole were added to a solution of 9.9 g (0.088 mol) of potassium tert.-butylate in 150 ml of tert.-butanol. The mixture was stirred at 40° C. for about 15 hours and was then diluted with toluene and water. The organic phase was separated off, washed with water, dried with sodium sulphate and filtered. The solvent was carefully distilled off from the filtrate under reduced pressure. 16.5 g (69% of theory) of 1-phenyl-5-tetrazolyloxyacetic acid 2-methyl-piperidide were obtained as the residue in the form of a light brown, viscous oil.

Elementary analysis: Calculated: C, 59.79%; H, 6.35%; N, 23.2%; O, 10.6%. Found: C, 59.6%; H, 6.5%; N, 22.3%; O, 10.3%.

The compounds of the formula (I) listed below could be prepared analogously to Example 1.

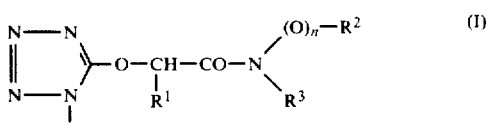
(I)

TABLE

| Example No. | R | $R^1$ | $-N \begin{matrix} (O)_n-R^2 \\ R^3 \end{matrix}$ | Refractive index ($n_D^{20}$) or melting point (°C.) |
|---|---|---|---|---|
| 2 | $C_6H_5$ | H | $-N \begin{matrix} OC_3H_7-iso \\ C_3H_7-iso \end{matrix}$ | 1.5672 |
| 3 | $C_6H_5$ | H | $-N(CH_2-CH=CH_2)_2$ | 79° C. |
| 4 | $C_6H_5$ | H | -N⟨hexahydroazepine⟩ | 1.5618 |
| 5 | $C_6H_5$ | H | $-N(CH_3)_2$ | 105° C. |
| 6 | $C_6H_5$ | H | $-N(C_2H_5)_2$ | 50° C. |
| 7 | $C_6H_5$ | H | -N⟨piperidine-CH_3⟩ | 131° C. |
| 8 | $C_6H_5$ | H | -N⟨3-methylpiperidine⟩ | 1.5572 |
| 9 | $C_6H_5$ | H | -N⟨2,6-dimethylpiperidine⟩ | 1.5464 |
| 10 | $C_6H_5$ | H | -N⟨morpholine⟩ | 110° C. |
| 11 | $C_6H_5$ | H | $-N(CH_2CH_2CH_3)_2$ | 39° C. |

TABLE-continued
| Example No. | R | R¹ | $-N\begin{matrix}(O)_n-R^2\\R^3\end{matrix}$ | Refractive index ($n_D^{20}$) or melting point (°C.) |
|---|---|---|---|---|
| 12 | C₆H₅ | H | $-N\begin{matrix}CH_2CH_3\\CH_2CH_2CH_2CH_3\end{matrix}$ | 1.5360 |
| 13 | C₆H₅ | H | $-N\begin{matrix}OCH_2CH_2-OC_2H_5\\C_3H_7-iso\end{matrix}$ | 1.5116 |
| 14 | C₆H₅ | H | 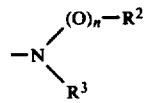 | 1.5469 |
| 15 | C₆H₅ | H | 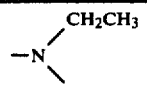 | 1.5482 |
| 16 | C₆H₅ | H | 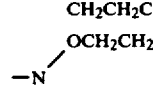 | 113° C. |
| 17 | C₆H₅ | H | 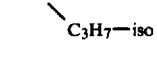 | 142° C. |
| 18 | C₆H₅ | H |  | 1.5394 |
| 19 | C₆H₅ | H | 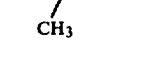 | 1.5389 |
| 20 | C₆H₅ | H | $-N\begin{matrix}OCH_3\\CH-CH_2-CH_3\\|\\CH_3\end{matrix}$ | 1.4783 |
| 21 | C₆H₅ | H | 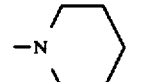 | 1.5397 |

TABLE-continued

| Example No. | R | R¹ | −N(O)ₙ−R² / R³ | Refractive index (n_D²⁰) or melting point (°C.) |
|---|---|---|---|---|
| 22 | $C_6H_5$ | H | −N(CH₂−C≡CH)(CH₂−C₆H₅) | 1.5770 |
| 23 | $C_6H_5$ | H | −N(C₂H₅)(C₆H₁₁) | 114° C. |
| 24 | $C_6H_5$ | H | −N(CH₂CH₂OCH₃)₂ | 1.5312 |
| 25 | $2,5\text{-}Cl_2\text{−}C_6H_3$ | H | −N(CH₃)(C₆H₅) | 1.5619 |
| 26 | $3,4\text{-}Cl_2\text{−}C_6H_5$ | H | −N(CH₃)(CH(CH₃)CH₂CH₃) | 1.5723 |
| 27 | $3,4\text{-}Cl_2\text{−}C_6H_3$ | H | −N(CH₃)(2-CH₃−C₆H₄) | 45-8° C. |
| 28 | $3,4\text{-}Cl_2\text{−}C_6H_3$ | H | 2-methylpiperidin-1-yl | 1.5801 |
| 29 | $C_6H_5$ | H | −N(CH₃)(2-CH₃-3-NO₂−C₆H₃) | 137° C. |
| 30 | $C_6H_5$ | H | 3-methylpiperidin-1-yl | 1.5477 |
| 31 | $C_6H_5$ | H | −N(CH₃)−CH₂C≡CH | 1.5298 |
| 32 | $3,5\text{-}(CF_3)_2\text{−}C_6H_3$ | H | −N(CH₃)−CH(CH₃)CH₂CH₃ | 1.4851 |
| 33 | $3,5\text{-}(CF_3)_2\text{−}C_6H_3$ | H | −N(CH₃)(C₆H₅) | 1.4992 |
| 34 | $3,5\text{-}(CF_3)_2\text{−}C_6H_3$ | H | −N(CH₂CH₂OCH₃)₂ | 82° C. |
| 35 | $3,4\text{-}Cl_2\text{−}C_6H_3$ | H | −N(CH₃)(C₆H₁₁) | 1.5480 |

TABLE-continued

| Example No. | R | R¹ | $-N\begin{smallmatrix}(O)_n-R^2\\R^3\end{smallmatrix}$ | Refractive index ($n_D^{20}$) or melting point (°C.) |
|---|---|---|---|---|
| 36 | C₆H₅ | H | −N(CH₃)−CH(CH₃)−C≡CH | 112° C. |
| 37 | 2,5-Cl₂−C₆H₃ | H | −N(morpholine with 2,6-diCH₃) | 1.5614 |
| 38 | 2,5-Cl₂−C₆H₃ | H | −N(CH₃)−C₆H₅ | 153° C. |
| 39 | 2,5-Cl₂−C₆H₃ | H | −N(CH₃)−CH(CH₃)CH₂CH₃ | 1.4991 |
| 40 | 2,5-Cl₂−C₆H₃ | H | −N(CH₃)−(2-CH₃−C₆H₄) | 134° C. |
| 41 | 3,5-(CF₃)₂−C₆H₃ | H | −N(C₂H₅)−C₆H₁₁ | 112° C. |
| 42 | 3,5-(CF₃)₂−C₆H₃ | H | −N(CH₂CH₂CH₃)−CH(CH₃)CH₂CH₃ | 1.5238 |
| 43 | 3,5-(CF₃)₂−C₆H₃ | H | −N(3-methylpiperidine) | 1.5015 |
| 44 | 3,5-(CF₃)₂−C₆H₃ | H | −N(2-methylpiperidine) | 1.5193 |
| 45 | 3,5-(CF₃)₂−C₆H₃ | H | −N(morpholine with 2,6-diCH₃) | 1.5316 |
| 46 | 3,5-(CF₃)₂−C₆H₃ | H | −N(CH₃)−C₆H₁₁ | 1.5419 |
| 47 | 2,5-Cl₂−C₆H₃ | H | −N(CH₂CH₂−OCH₃)₂ | 1.5298 |

| Example No. | R | R¹ | $(O)_n-R^2$ / $-N$ / $R^3$ | Refractive index ($n_D^{20}$) or melting point (°C.) |
|---|---|---|---|---|
| 48 | 2,5-Cl$_2$—C$_6$H$_3$ | H | −N(C$_2$H$_5$)−C$_6$H$_{11}$ | 1.5085 |
| 49 | 2,9-Cl$_2$—C$_6$H$_3$ | H | −N(3-methylpiperidinyl) | 130–3° C. |
| 50 | 3-CF$_3$—C$_6$H$_4$ | H | −N(CH$_3$)—CH(CH$_3$)—CH$_2$CH$_3$ | 1.4993 |
| 51 | 3-CF$_3$—C$_6$H$_4$ | H | −N(2,6-dimethylmorpholinyl) | 1.5207 |
| 52 | 3-CF$_3$—C$_6$H$_4$ | H | −N(CH$_3$)—C$_6$H$_5$ | 1.5082 |
| 53 | 3-NO$_2$—C$_6$H$_4$ | H | −N(2-methylpiperidinyl) | 124° C. |
| 54 | 3-NO$_2$—C$_6$H$_4$ | H | −N(CH$_3$)—C$_6$H$_{11}$ | 1.5411 |
| 55 | 3-NO$_2$—C$_6$H$_4$ | H | −N(CH$_2$CH$_2$CH$_3$)−CH(CH$_3$)CH$_2$CH$_3$ | 1.5332 |
| 56 | 3-CF$_3$—C$_6$H$_4$ | H | −N(CH$_3$)—C$_6$H$_{11}$ | 1.5335 |
| 57 | 3-CF$_3$—C$_6$H$_4$ | H | −N(3-methylpiperidinyl) | 96° C. |
| 58 | 3-CF$_3$—C$_6$H$_4$ | H | −N(CH$_3$)—(CH$_2$)$_3$—CH$_3$ | 1.4985 |
| 59 | 3-CF$_3$—C$_6$H$_4$ | H | −N(CH$_2$CH$_2$CH$_3$)−CH(CH$_3$)—CH$_2$CH$_3$ | 1.4960 |

TABLE-continued

| Example No. | R | R¹ | -N((O)ₙ-R²)(R³) | Refractive index (n_D²⁰) or melting point (°C.) |
|---|---|---|---|---|
| 60 | 2,5-Cl₂—C₆H₃ | H | -N(CH₂CH₂CH₃)(CH(CH₃)-CH₂CH₃) | 1.5500 |
| 61 | 2,5-Cl₂—C₆H₃ | H | -N(CH₂-C≡CH)(CH₂-C₆H₅) | 1.4979 |
| 62 | 3-CF₃—C₆H₄ | H | -N(CH₃)(2-CH₃-C₆H₄) | 1.5162 |
| 63 | 3-CF₃—C₆H₄ | H | 2-methylpiperidin-1-yl | 1.5180 |
| 64 | 3-CF₃—C₆H₄ | H | -N(C₂H₅)(C₆H₁₁) | 1.5135 |
| 65 | 3-CF₃—C₆H₄ | H | -N(CH₂CH₂OCH₃)₂ | 1.4958 |
| 66 | 2,5-Cl₂—C₆H₃ | H | -N(CH₃)(C₆H₁₁) | 110° C. |
| 67 | 2,5-Cl₂—C₆H₃ | H | -N(CH₂CH₃)((CH₂)₃CH₃) | 1.5436 |
| 68 | 2,5-Cl₂—C₆H₃ | H | 2-methylpiperidin-1-yl | 1.5509 |
| 69 | 3-NO₂—C₆H₄ | H | -N(CH₃)(CH(CH₃)-CH₂CH₃) | 1.5472 |
| 70 | 3-NO₂—C₆H₄ | H | -N(CH₃)((CH₂)₃CH₃) | 1.5398 |
| 71 | 3-NO₂—C₆H₄ | H | -N(CH₃)(2-CH₃-C₆H₄) | 140° C. |

TABLE-continued

| Example No. | R | R¹ | $-N\begin{smallmatrix}(O)_n-R^2\\R^3\end{smallmatrix}$ | Refractive index ($n_D^{20}$) or melting point (°C.) |
|---|---|---|---|---|
| 72 | 3-NO$_2$—C$_6$H$_4$ | H | —N(CH$_2$—C≡CH)(CH$_2$—C$_6$H$_5$) | 1.5462 |
| 73 | 3-NO$_2$—C$_6$H$_4$ | H | —N(CH$_2$CH$_2$OCH$_3$)$_2$ | 1.5437 |
| 74 | 3-NO$_2$—C$_6$H$_4$ | H | —N(CH$_2$CH$_3$)(C$_6$H$_{11}$) | 1.5388 |
| 75 | 3-NO$_2$—C$_6$H$_4$ | H | 2,6-dimethylmorpholino | 83° C. |
| 76 | 4-CH$_3$—C$_6$H$_4$ | H | —N(CH$_3$)(C$_6$H$_5$) | 99° C. |
| 77 | 4-CH$_3$—C$_6$H$_4$ | H | —N(CH$_3$)(2-CH$_3$—C$_6$H$_4$) | 129–132° C. |
| 78 | 4-CH$_3$—C$_6$H$_4$ | H | —N(CH$_2$CH$_2$OCH$_3$)$_2$ | 95° C. |
| 79 | 2-Cl—6-CH$_3$—C$_6$H$_3$ | H | —N(CH$_3$)—CH(CH$_3$)—CH$_2$CH$_3$ | 1.5350 |
| 80 | 2-Cl—6-CH$_3$—C$_6$H$_3$ | H | —N(CH$_3$)—CH(CH$_3$)—C≡CH | 130° C. |
| 81 | 2-Cl—6-CH$_3$—C$_6$H$_3$ | H | —N(CH$_2$C≡CH)(CH$_2$—C$_6$H$_5$) | 137° C. |
| 82 | 2-Cl—6-CH$_3$—C$_6$H$_3$ | H | —N(CH$_2$CH$_2$OCH$_3$)$_2$ | 1.5303 |
| 83 | 2-Cl—6-CH$_3$—C$_6$H$_3$ | H | 2,6-dimethylmorpholino | 1.5469 |
| 84 | 2-Cl—6-CH$_3$—C$_6$H$_3$ | H | —N(CH$_3$)(2-CH$_3$—C$_6$H$_4$) | 144° C. |
| 85 | 2-Cl—6-CH$_3$—C$_6$H$_3$ | H | —N(CH$_3$)(C$_6$H$_{11}$) | 173° C. |

TABLE-continued

| Example No. | R | R¹ | (O)$_n$—R²<br>—N<br>R³ | Refractive index (n$_D^{20}$) or melting point (°C.) |
|---|---|---|---|---|
| 86 | 2-Cl—6-CH$_3$—C$_6$H$_3$ | H | —N(CH$_2$CH$_3$)(CH$_2$-C$_6$H$_{11}$) | 44° C. |
| 87 | 4-Cl—2-CH$_3$—C$_6$H$_3$ | H | 2,6-dimethylmorpholino | 65° C. |
| 88 | 4-Cl—2-CH$_3$—C$_6$H$_3$ | H | —N(CH$_3$)—CH(CH$_3$)—C≡CH | 116° C. |
| 89 | 4-Cl—2-CH$_3$—C$_6$H$_3$ | H | —N(CH$_3$)—CH(CH$_3$)—CH$_2$CH$_3$ | 1.5478 |
| 90 | 4-Cl—2-CH$_3$—C$_6$H$_3$ | H | —N(CH$_2$CH$_2$OCH$_3$)$_2$ | 1.5431 |
| 91 | 4-Cl—2-CH$_3$—C$_6$H$_3$ | H | —N(CH$_3$)—(2-CH$_3$-C$_6$H$_4$) | 152° C. |
| 92 | 4-Cl—2-CH$_3$—C$_6$H$_3$ | H | —N(CH$_3$)—C$_6$H$_{11}$ | 1.5423 |
| 93 | 4-Cl—2-CH$_3$—C$_6$H$_3$ | H | —N(CH$_2$CH$_3$)—C$_6$H$_{11}$ | 1.5395 |
| 94 | 4-Cl—2-CH$_3$—C$_6$H$_3$ | H | —N(CH$_2$CH$_2$CH$_3$)—CH(CH$_3$)—CH$_2$CH$_3$ | 1.5331 |
| 95 | 4-Cl—2-CH$_3$—C$_6$H$_3$ | H | —N(CH$_3$)—(CH$_2$)$_3$—CH$_3$ | 1.5430 |
| 96 | 4-Cl—2-CH$_3$—C$_6$H$_3$ | H | —N(CH$_2$CH$_3$)—(CH$_2$)$_3$—CH$_3$ | 1.5382 |
| 97 | C$_6$H$_5$ | H | —N(CH$_3$)—C$_6$H$_5$ | 153 |
| 98 | C$_6$H$_5$ | H | —N(CH$_3$)—(2-CH$_3$-C$_6$H$_4$) | 139–141 |
| 99 | C$_6$H$_5$ | H | —N(CH$_3$)—CH(CH$_3$)—CH$_2$CH$_3$ | 1.5291 |

TABLE-continued
| Example No. | R | R¹ | $-N\begin{matrix}(O)_n-R^2\\R^3\end{matrix}$ | Refractive index ($n_D^{20}$) or melting point (°C.) |
|---|---|---|---|---|
| 100 | $C_6H_5$ | H | 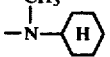 | 116 |
| 101 | $C_6H_5$ | H | 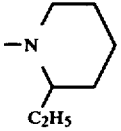 | 1.5237 |
| 102 | $C_6H_5$ | H | 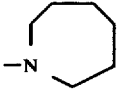 | 1.5409 |
| 103 | $C_6H_5$ | H | 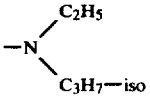 | 1.5385 |
| 104 | $C_6H_5$ | H | 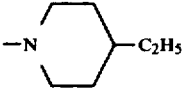 | 1.5465 |
| 105 | $3,5-(CF_3)_2C_6H_3$ | H | 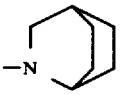 | 89 |
| 106 | $2,4-Cl_2-C_6H_3$ | H | 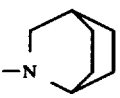 | 142 |
| 107 | $3-CF_3-C_6H_4$ | H | 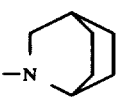 | 69 |
| 108 | $C_6H_5$ | H | 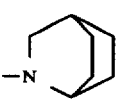 | 110 |
| 109 | $3-NO_2-C_6H_4$ | H | 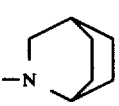 | 152 |
| 110 | $2,5-Cl_2-C_6H_3$ | H |  | 123 |
| 111 | $2,4-Cl_2-C_6H_3$ | H | 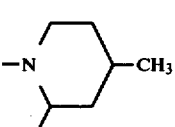 | 1.5543 |

TABLE-continued

| Example No. | R | R¹ | $-N\begin{matrix}(O)_n-R^2\\R^3\end{matrix}$ | Refractive index ($n_D^{20}$) or melting point (°C.) |
|---|---|---|---|---|
| 112 | 2,4-Cl₂—C₆H₃ | H | 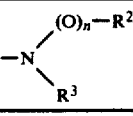 2-ethylpiperidin-1-yl | 1.5575 |
| 113 | 2,4-Cl₂—C₆H₃ | H | 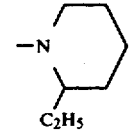 4-ethylpiperidin-1-yl | 1.5542 |
| 114 | 2,4-Cl₂—C₆H₃ | H | $-N\begin{matrix}C_2H_5\\C_3H_7-iso\end{matrix}$ | 1.5433 |
| 115 | 3-CF₃—C₆H₄ | H | 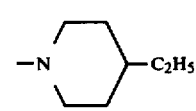 2,4-dimethylpiperidin-1-yl | 1.5054 |
| 116 | 3-CF₃—C₆H₄ | H | 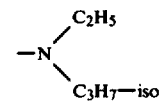 2-ethylpiperidin-1-yl | 1.5029 |
| 117 | 3-CF₃—C₆H₄ | H | 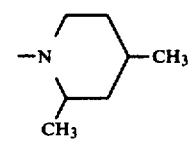 4-ethylpiperidin-1-yl | 1.5065 |
| 118 | 3-CF₃—C₆H₄ | H | $-N\begin{matrix}C_2H_5\\C_3H_7-iso\end{matrix}$ | 1.4923 |
| 119 | 2-CH₃—4-Cl—C₆H₃ | H | 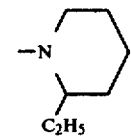 4-ethylpiperidin-1-yl | 120 |
| 120 | 2-CH₃—4-Cl—C₆H₃ | H | 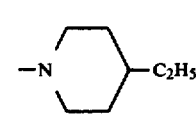 4-ethyl-2-methylpiperidin-1-yl | 1.5397 |
| 121 | 2-CH₃—4-Cl—C₆H₃ | H | 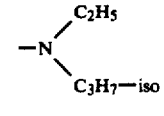 2,4-dimethylpiperidin-1-yl | 1.5389 |
| 122 | 2-CH₃—4-Cl—C₆H₃ | H | 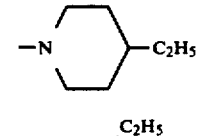 2-ethylpiperidin-1-yl | 1.5475 |

TABLE-continued
| Example No. | R | R¹ | $-N\begin{matrix}(O)_n-R^2\\R^3\end{matrix}$ | Refractive index ($n_D^{20}$) or melting point (°C.) |
|---|---|---|---|---|
| 123 | 2-CH₃—4-Cl—C₆H₃ | H | 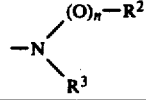 | 111 |
| 124 | 2-CH₃—4-Cl—C₆H₃ | H | 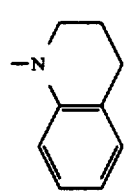 | 141 |
| 125 | C₆H₅ | H | 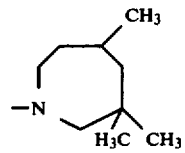 | (Oil) |
| 126 | 2,5-(CF₃)₂—C₆H₃ | H | 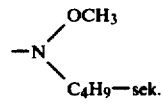 | (Oil) |
| 127 | 2-Cl—6-CH₃—C₆H₃ | H | 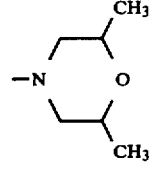 | 161 |
| 128 | 2-Cl—6-CH₃—C₆H₃ | H | 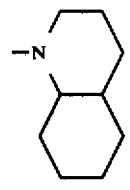 | 146 |
| 129 | 2-Cl—6-CH₃—C₆H₃ | H | 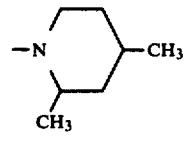 | 126 |
| 130 | 2-Cl—6-CH₃—C₆H₃ | H | 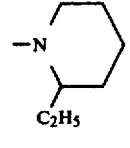 | 1.5372 |
| 131 | 2-Cl—6-CH₃—C₆H₃ | H | 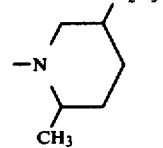 | 86 |

The compounds of the formula (II) to be used as starting substances could be prepared as follows:

EXAMPLE a

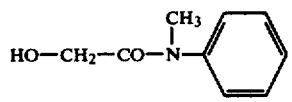

A suspension of 183.5 g (1 mol) of chloro-acetic acid N-methylanilide, 82 g (1 mol) of anhydrous sodium acetate and 320 ml of toluene was heated to 115°–120° C. for 4 hours and was then cooled to room temperature. The mixture was filtered and the residue was rinsed with cold toluene. After distilling off the solvent from the toluene solution and evaporating the residue in a vapour-pump vacuum at a bath temperature of 80°–85° C., 207 g of α-acetoxy-acetic acid N-methylanilide, which crystallised on standing, were obtained; purity according to gas chromatography: 98%; melting point: 54°–56° C.; yield: 99% of theory.

The reaction mixture obtained from 211.2 g (1 mol) of α-acetoxyacetic acid N-methylanilide (98% pure), 0.2 g of sodium hydroxide and 160 g of methanol was heated under reflux for 4 hours. The mixture of methanol and methyl acetate was distilled off. The liquid distillation residue: 170 g yield of hydroxyacetic acid N-methylanilide (quantitative, purity according to the gas chromatogram: 98%; melting point: 52°–53° C., solidified on cooling).

The compounds below, of the formula (II), were obtained analogously:

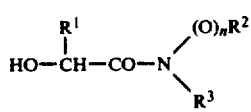

(II)

| Example | R$^1$ | $-N\begin{smallmatrix}(O)_n-R^2\\R^3\end{smallmatrix}$ | Melting point (°C.) or refractive index |
|---|---|---|---|
| b | H | -N(H)(CH$_3$)(cyclohexyl) | 36 |
| c | H | —N(CH$_2$—CH$_2$—OCH$_3$)$_2$ | n$_D^{25}$: 1.4662 |
| d | H | -N(CH$_3$)(C$_6$H$_{11}$) | 83 |
| e | H | —N(CH$_3$)—CH(CH$_3$)—C≡CH | n$_D^{25}$: 1.4859 |
| f | H | -N(piperidinyl with CH$_3$) | n$_D^{23}$: 1.4816 |
| g | H | -N(H)(decahydronaphthyl) | 55 |
| h | H | -N(H)(decahydronaphthyl) | n$_D^{23}$: 1.5076 |
| i | H | -N(H)(tetrahydroquinolinyl) | 80 |
| j | H | -N(H)(CH$_3$-decahydronaphthyl) | — |

| Example | R$^1$ | $-N\begin{smallmatrix}(O)_n-R^2\\R^3\end{smallmatrix}$ | Melting point (°C.) or refractive index bp. = boiling point |
|---|---|---|---|
| k | H | —N(OCH$_3$)(CH$_3$) | n$_D^{22}$: 1.4583 bp: 47° C./0.133 bar |
| l | H | —N(OCH$_2$CH$_2$—OC$_2$H$_5$)(C$_3$H$_7$—iso) | n$_D^{24}$: 1.4485 |
| m | H | —N(OC$_3$H$_7$—iso)(C$_3$H$_7$—iso) | n$_D^{21}$: 1.4475 |
| n | H | —N(OCH$_2$CH=CH$_2$)(CH$_2$—CH=CH$_2$) | n$_D^{23}$: 1.4793 bp: 76–78° C./ 0.0133 bar |

The halogenotetrazoles of the formula (III) to be used as starting substances could be prepared, for example, as follows:

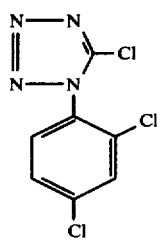

A solution of 243 g (1.0 mol) of 2,4-dichlorophenyl isocyanide dichloride in 800 ml of acetone was added dropwise to a solution of 65 g (1.0 mol) of sodium azide in 1 liter of water. The reaction mixture was stirred at 50° C. for 30 minutes and under reflux for a further 30 minutes, cooled, poured into water and filtered. 243 g (97% of theory) of 5-chloro-1-(2,4-dichlorophenyl-(1H)-tetrazole of melting point 81° C. were obtained.

The following compound was obtained analogously:

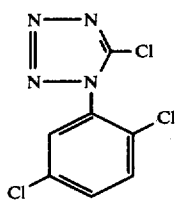

Melting point: 122° C.

It will be understood that the specification and examples are illustrative, but not limitative of the present invention and that other embodiments wherein the spirit and scope of the invention will suggest themselves to those skilled in the art.

What is claimed is:

1. A tetrazolyloxycarboxylic acid amide of the formula

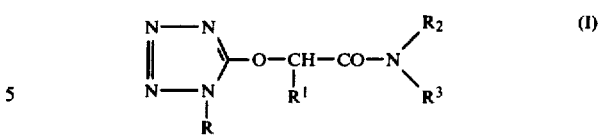

wherein

R is phenyl, mono chlorophenyl or dichlorophenyl, $R^1$ is hydrogen, $R^2$ is $C_1$-$C_6$-alkyl, allyl, propargyl, 1-methyl-propargyl, 1,1-dimethyl-propargyl, cyclohexyl, benzyl or phenyl, and $R^3$ is $C_1$-$C_6$-alkyl or allyl or $R^2$ and $R^3$ together with the nitrogen atom to which they are bonded, represent piperidyl, monoalkyl or dialkyl substituted piperidyl with 1 to 3 carbon atoms per alkyl group or perhydroazepinyl.

2. Tetrazolyloxycarboxylic acid amide compound as claimed in claim 1 wherein R is phenyl.

3. Tetrazolyloxycarboxylic acid amide compound as claimed in claim 1 wherein $R^2$ is methyl.

4. Tetrazolyloxycarboxylic acid amide compound as claimed in claim 1 wherein $R^3$ is methyl and $R^2$ is $C_1$-$C_6$ alkyl, allyl, propargyl, 1-methyl-propargyl cyclohexyl, benzyl or phenyl.

5. Tetrazolyloxycarboxylic acid amide compound as claimed in claim 1 designated 1-phenyl-5-tetrazolyloxyacetic acid diallylamide.

6. Tetrazolyloxycarboxylic acid amide compound as claimed in claim 1 designated 1-phenyl-5-tetrazolyloxyacetic acid hexamethylene-amide.

7. Tetrazolyloxycarboxylic acid amide compound as claimed in claim 1 designated 1-phenyl-5-tetrazolyloxyacetic acid 3-methyl-piperidide.

8. Tetrazolyloxycarboxylic acid amide compound as claimed in claim 1 designated 1-phenyl-5-tetrazolyloxyacetic acid 2-ethyl-piperidide.

9. Tetrazolyloxycarboxylic acid amide compound as claimed in claim 1 designated 1-phenyl-5-tetrazolyloxyacetic acid N-methyl-anilide.

10. Tetrazolyloxycarboxylic acid amide compound as claimed in claim 1 wherein $R^3$ is methyl.

* * * * *